United States Patent
Johansson et al.

(10) Patent No.: US 9,629,946 B2
(45) Date of Patent: Apr. 25, 2017

(54) POLYMERIC PROTECTIVE LAYER

(75) Inventors: Anders Johansson, Uppsala (SE); Marten Rooth, Uppsala (SE)

(73) Assignee: NANEXA AB, Uppsala (SE)

( * ) Notice: Subject to any disclaimer, the term of this patent is extended or adjusted under 35 U.S.C. 154(b) by 0 days.

(21) Appl. No.: 13/824,398

(22) PCT Filed: Sep. 13, 2011

(86) PCT No.: PCT/SE2011/051103
§ 371 (c)(1),
(2), (4) Date: Mar. 18, 2013

(87) PCT Pub. No.: WO2012/036618
PCT Pub. Date: Mar. 22, 2012

(65) Prior Publication Data
US 2013/0280471 A1 Oct. 24, 2013

(30) Foreign Application Priority Data
Sep. 17, 2010 (SE) ...................................... 1050970

(51) Int. Cl.
*A61L 31/16* (2006.01)
*B29C 70/68* (2006.01)
(Continued)

(52) U.S. Cl.
CPC ............... *A61L 31/16* (2013.01); *A61L 27/34* (2013.01); *A61L 27/54* (2013.01); *A61L 29/085* (2013.01);
(Continued)

(58) Field of Classification Search
CPC .. B32B 1/02; B32B 1/08; B32B 27/18; Y10T 428/1352; Y10T 428/1372; Y10T 428/1376; Y10T 428/1379; Y10T 428/1386; Y10T 428/139; Y10T 428/1393; B29C 70/68; A61L 31/16; A61L 2300/404
(Continued)

(56) References Cited

U.S. PATENT DOCUMENTS 4,191,743 A 3/1980 Klemm et al.
5,679,399 A 10/1997 Shlenker et al.
(Continued)

FOREIGN PATENT DOCUMENTS

WO 02/062577 A1 8/2002
WO 2005/014074 A1 2/2005
(Continued)

OTHER PUBLICATIONS

Revised International Search Report, dated Mar. 12, 2012, from corresponding PCT application.
(Continued)

*Primary Examiner* — Walter B Aughenbaugh
(74) *Attorney, Agent, or Firm* — Young & Thompson

(57) ABSTRACT

A polymeric product including at least two layers, wherein a functional layer includes a polymeric material and at least one anti-microbial substance, and a protective layer, including a polymeric material arranged outside the functional layer and completely covering the functional layer, wherein the protective layer does not include any anti-microbial substances. A method of producing the product, the use of the same and a kit for producing the product.

16 Claims, 3 Drawing Sheets

(51) Int. Cl.

| | |
|---|---|
| *B32B 1/02* | (2006.01) |
| *B32B 27/18* | (2006.01) |
| *B32B 1/08* | (2006.01) |
| *A61L 27/34* | (2006.01) |
| *A61L 27/54* | (2006.01) |
| *A61L 29/08* | (2006.01) |
| *A61L 29/16* | (2006.01) |
| *B32B 25/04* | (2006.01) |
| *B32B 25/08* | (2006.01) |
| *B32B 27/08* | (2006.01) |
| *B32B 27/20* | (2006.01) |
| *C08K 3/08* | (2006.01) |
| *C08K 5/00* | (2006.01) |

(52) U.S. Cl.
CPC .............. *A61L 29/16* (2013.01); *B29C 70/68* (2013.01); *B32B 1/02* (2013.01); *B32B 1/08* (2013.01); *B32B 25/042* (2013.01); *B32B 25/08* (2013.01); *B32B 27/08* (2013.01); *B32B 27/18* (2013.01); *B32B 27/20* (2013.01); *A61L 2300/104* (2013.01); *A61L 2300/404* (2013.01); *A61L 2400/12* (2013.01); *A61L 2420/04* (2013.01); *B32B 2264/105* (2013.01); *B32B 2274/00* (2013.01); *B32B 2307/7145* (2013.01); *B32B 2535/00* (2013.01); *B32B 2581/00* (2013.01); *C08K 3/08* (2013.01); *C08K 5/0058* (2013.01); *Y10T 428/139* (2015.01); *Y10T 428/1352* (2015.01); *Y10T 428/1372* (2015.01); *Y10T 428/1376* (2015.01); *Y10T 428/1379* (2015.01); *Y10T 428/1386* (2015.01); *Y10T 428/1393* (2015.01); *Y10T 428/239* (2015.01)

(58) Field of Classification Search
USPC .......... 428/35.7, 36.4, 36.5, 36.6, 36.8, 36.9, 428/36.91
See application file for complete search history.

(56) References Cited

U.S. PATENT DOCUMENTS

| | | | |
|---|---|---|---|
| 5,756,145 A | 5/1998 | Darouiche | |
| 5,902,283 A | 5/1999 | Darouiche et al. | |
| 6,887,270 B2* | 5/2005 | Miller et al. | 623/11.11 |
| 6,921,502 B1* | 7/2005 | Nord et al. | 264/46.4 |
| 2002/0082340 A1 | 6/2002 | Hanke et al. | |
| 2004/0249441 A1 | 12/2004 | Miller et al. | |
| 2005/0107870 A1 | 5/2005 | Wang et al. | |
| 2005/0164169 A1* | 7/2005 | Malak | 435/5 |
| 2008/0138385 A1 | 6/2008 | Fukatsu et al. | |
| 2008/0147019 A1* | 6/2008 | Song | C08B 37/003 604/265 |
| 2008/0181931 A1* | 7/2008 | Qiu | A61L 12/088 424/429 |
| 2009/0202609 A1* | 8/2009 | Keough | A61L 31/10 424/426 |

FOREIGN PATENT DOCUMENTS

| | | |
|---|---|---|
| WO | 2007/017019 A2 | 2/2007 |
| WO | 2008/094876 A1 | 8/2008 |
| WO | 2009/045455 A1 | 4/2009 |
| WO | 2010/068985 A1 | 6/2010 |

OTHER PUBLICATIONS

European Search Report, dated Apr. 24, 2015, from corresponding European application.

* cited by examiner

POLYMERIC PROTECTIVE LAYER

TECHNICAL FIELD

The present invention relates to a polymeric product constituted in such a way that the ingrowth of fungal or other microbial substances is hindered; a method of producing said product and the use of the same. The present invention further relates to a kit for making said product.

BACKGROUND OF THE INVENTION

Many polymeric products used today, both indoors and outdoors, as sealing or insulation material, gasket, membrane, valves or filters; as well as the polymeric products used in in vivo applications such as implants and various devices are exposed to microorganisms. These organisms adhere to the polymeric material and proliferate. Fungal development on the surface of the polymeric material can lead to fungal penetration into the material. Over time, this penetration may lead to crack formation which will limit the function of the material and in the worse case collapse of the material, FIG. 1.

This scenario would lead to that the material loses its mechanical properties and would need to be replaced. For in vivo applications this causes additional surgical procedures which are both unpleasant for the patient and expensive for the society.

Prevention of microbial adherence and proliferation on objects and surfaces has been studied and known for many years. To coat or impregnate the objects with substances that are released in a sustained manner have been known and tested for a long time. However the drawbacks are that the release is sometimes to fast and the effect vanishes. The anti-microbial effect of silver and copper for example has been known for centuries but has never been fully understood. These substances could be in form of pure metal, ions or conjugates.

Prior art presents several ways of hindering the ingrowth of fungal and other microorganisms into polymeric materials, both thermoplastics and thermosets. WO2009/045455 presents an implantable medical device comprising a thermoplastic or a thermoset treated with gentian violet (hexamethyl pararosaniline chloride). The device could contain additional anti-microbial agents such as metal salts or conjugates of for example silver, copper, bismuth, gallium and zinc.

WO2008/094876 and WO2005/014074 present polymeric medical devices, especially contact lenses, with anti-microbial properties obtained by the addition of silver nanoparticles to various polymeric materials. The anti-microbial material is obtained by forming the silver nanoparticles in situ when polymerizing the polymeric material leaving an evenly distributed silver nanoparticle device.

WO2007/017019 presents anti-microbial catheters comprising a polymer matrix and an aggregation of inorganic pigment and silver acetate. The latter combination acts as an anti-microbial agent. The inorganic pigment may further comprise one or more layers in order to obtain various optical properties.

However, some of these anti-microbial substances are controversial in respect of their toxicity to humans and animals, and their environmental harmfulness. Nanoparticles for example have been a topic of debates concerning its potential toxicity. For example silver nanoparticles have been shown to cause argyria (bluish-grey coloration of the skin) and argyrosis (discoloration of eyes). Additionally, exposure to soluble silver may cause toxic effects on to liver and kidney, irritation in the eyes, respiratorial and intestinal tract and blood cell changes. Additionally, the anti-microbial substances usually have no ability to distinguish between malign and benign bacteria and therefore kill sometimes benign and essential bacteria.

SUMMARY OF THE INVENTION

The object of the present invention is to provide a polymeric product comprising a functional layer containing an anti-microbial substance and a protective layer covering the functional layer; a method of producing said product; the use of the same and a kit for producing the product.

In a first aspect, the invention provides a polymeric product.

In one embodiment of the present invention the anti-microbial substance in the functional layer comprises metal nanoparticles for example silver and/or copper nanoparticles, preferably silver nanoparticles.

In another embodiment of the present invention the polymeric materials in the layers are rubber and/or thermoplastic elastomer.

In another embodiment of the present invention the protective layer has a thickness of between 1-100 µm, preferably between 1-50 µm.

In yet another embodiment the polymeric material in the layers is the same.

In yet another embodiment the polymeric material in at least one of the layers is selected from the group consisting of natural, silicone, isoprene, styrene-butadien, styrene-ethylene, butadiene, butyl, ethylene-propylene, nitrile, acrylic, chloroprene, fluoro silicone, nitrile butadiene, methyl vinyl silicone or urethane rubber, but preferably silicone rubber.

In another embodiment of the present invention the polymeric material in at least one of the layers is selected from the group consisting of polyester, polyethers, polyamines, polyamides, polyurethanes, polysiloxanes, polypropylenes, polycarbonates, polyacrylates, polyvinyls, polyethylenes, polyimides, polysulfones, polyfenyloxides, polyacetals, polycellulose and polystyrene.

In a second aspect the present invention relates to a method of producing a polymeric product according to the present invention comprising the steps of:
   a) providing a first polymeric material containing an anti-microbial substance
   b) forming a functional layer comprising the first polymeric material;
   c) optionally curing the functional layer;
   d) providing, on said functional layer, a protective layer completely covering said functional layer, wherein the protective layer comprising a polymeric material does not comprise any anti-microbial substances;
   e) optionally cure the protective layer; and optionally
   f) repeating step d and e to provide additional layers.

In one embodiment the functional layer is provided using dip coating, spin coating, spraying, extruding, blowing or moulding techniques In one embodiment the protective layer is provided using dip coating, spin coating, spraying, compression or injection moulding or wherein the protective layer is preformed and then applied on the functional layer.

In yet another embodiment the functional layer is formed using injection moulding, compression moulding, injection reaction moulding, transfer moulding, blow moulding, rotational moulding, film blowing, rotational blowing or calendering.

In yet another embodiment the anti-microbial substance is metal nanoparticles, for example silver and/or copper nanoparticles.

In a third aspect the present invention provides a kit for preparing the polymeric product containing a plurality of components for making the layers making up the product, wherein
- a first set of components comprise a polymeric material, an anti-microbial substance for producing the functional layer, and
- a second set of components comprise a polymeric material for producing the protective layer.

In one embodiment the polymeric material is provided in a suitable solvent.

In another embodiment the first and/or the second set of components further comprises a curing agent.

In another embodiment the anti-microbial substance is nanoparticles, preferably silver nanoparticles.

In yet another embodiment the polymeric materials in the first and second set of components are the same.

A fourth aspect is the use of the polymeric product of the present invention for in vivo applications.

In one embodiment the application is voice membrane or prostheses, heart valves, joints, lenses, tendons, breast implants, catheters or as an insulation material.

In another embodiment the product is used as a sealing or insulation material, gasket, membrane, valves or filters.

DETAILED DESCRIPTION OF THE INVENTION

In the present invention, the term "anti-microbial substance" refers to a substance that kills or inhibits growth of microorganisms such as fungi, bacteria and protozoans.

In the present invention the term "conjugate" includes chemical substances wherein the comprised atoms are bonded to each other.

In order to overcome the drawbacks of prior art the present invention provides a polymeric product comprising at least two layers, a functional layer and a protective layer. The functional layer comprises a thermoplastic or a thermoset material and an anti-microbial substance, for example silver nanoparticles. Completely covering the functional layer is a protective layer also comprising a thermoplastic or a thermoset but lacks the anti-microbial substance. This construction allows the product to be protected from microbial attacks but the patient, in an in vivo application, or the surroundings and the environment, is not exposed to the potentially toxic or harmful anti-microbial substance. Prior art today are focused on the protection of the product itself and/or to expose the patients to the anti-microbial substance for therapeutical reasons, while the present invention adds the feature of protecting the surrounding environment.

Figure 1:
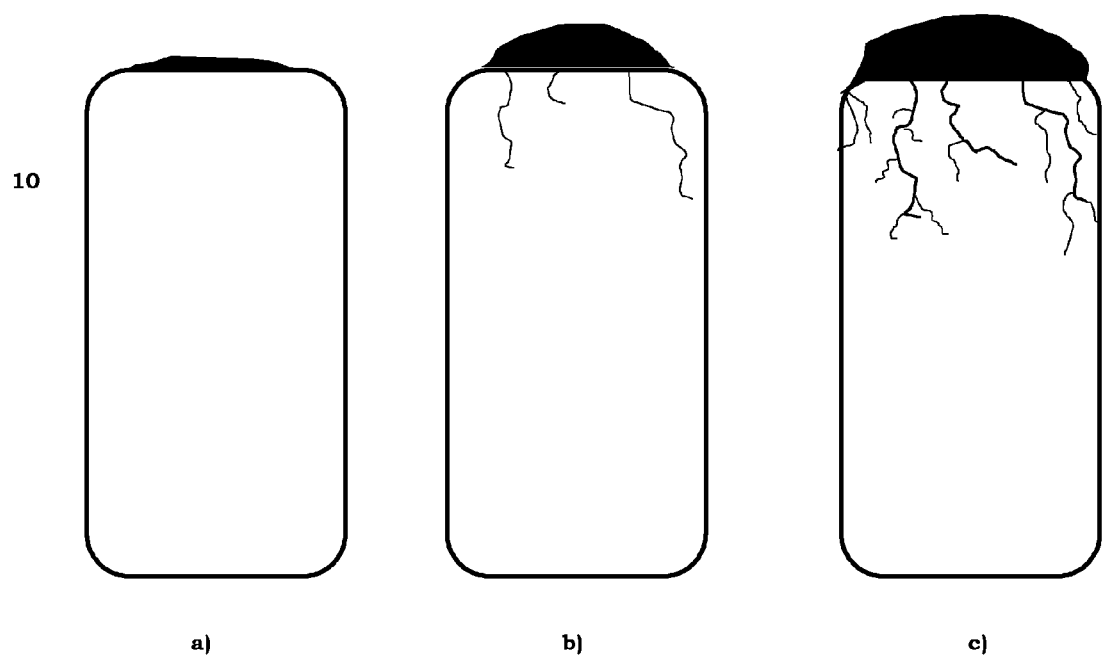
FIG. 1, a schematic picture of a product under microbial attack and ingrowth.
Figure 2:
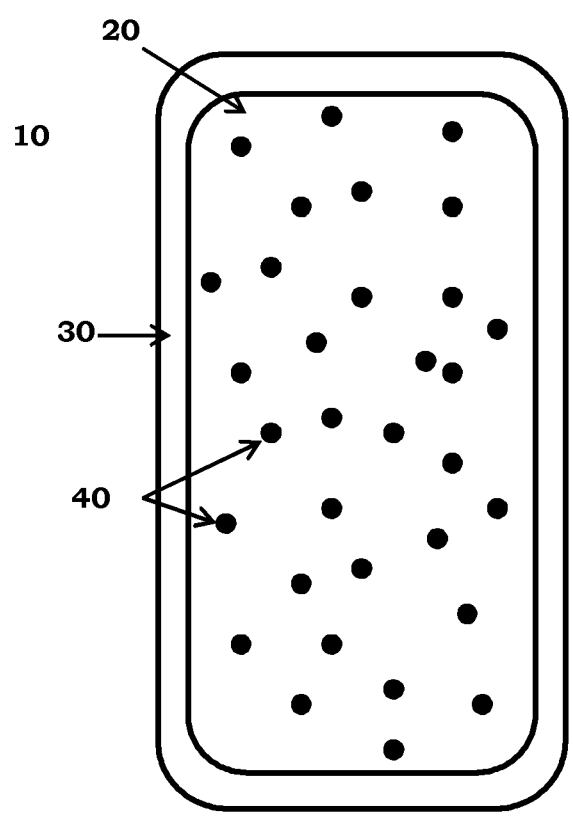
FIG. 2, a schematic picture of an embodiment according to the present invention.

FIG. 2 illustrates schematically the present invention wherein a polymeric product 10 comprises an outer protective layer 30 which shields the patient or the surroundings from the potentially toxic substance. The functional layer 20 comprising an anti-microbial substance 40 protects the product 10 from the degradation caused by a microbial attack and ingrowth.

In a preferred embodiment, the protective layer, completely covering the functional layer, is substantially made of the same polymeric material as the functional layer. This is to obtain the same mechanical property for the whole construction. This could also be achieved by using different polymeric materials but then the mechanical properties should be similar.

The polymeric material could be any material suitable for the application depending on the wanted properties. Both organic and inorganic polymers can be used. The material could be either cross-linked or non-cross-linked, a homo or hetero polymer, a co-polymer, grafted or branched polymer.

Thermoplastic polymers that could be used may be selected from, but not limited to, polyester, polyethers, polyamines, polyamides, polyurethanes, polysiloxanes, polypropylenes, polycarbonates, polyacrylates, polyvinyls, polyethylenes, polyimides, polysulfones, polyfenyloxides, polyacetals, polycellulose, polyoleophines and polystyrene or combinations thereof.

If the product comprises a rubber, a thermoset, it is preferably but not limited to natural, silicone, isoprene, styrene-butadien, styrene-ethylene, butadiene, butyl, ethylene-propylene, nitrile, acrylic, chloroprene, fluoro silicone, nitrile butadiene, methyl vinyl silicone or urethane rubber, or combinations thereof, but most preferably silicone rubber.

Figure 3:
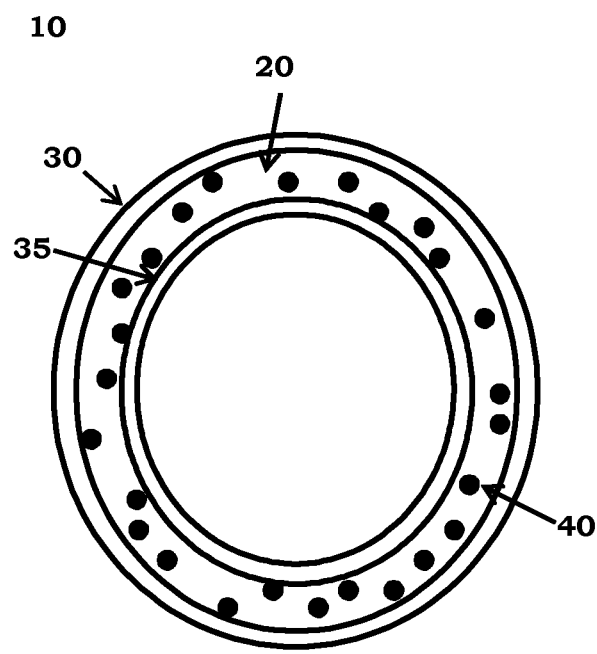
FIG. 3, a schematic cross-section view of another embodiment according to the present invention.

The product could also comprise of more than two layers where the functional layer 20 is a layer formed between two protective layers 30 and 35. This embodiment could be used for tubes or pipes where the microbial attack can come from both sides of the functional layer. This embodiment is schematically illustrated in FIG. 3.

Many substances exhibit anti-microbial properties and a person skilled in the art knows what substances are suitable for the specific application. These substances include but are not limited to various acids, such as lactic acid, citric acid and acetic acid; or essential oils such as mint oil, lemon oil, onion oil, eucalyptus oil and cinnamon oil; or heavy metal cations such as $Hg^{2+}$, $Cu^{2+}$ and $Pb^{2+}$; or peptides such as peptides with multiple lysine and arginine residues and which exhibit an amphipathic nature; and metal nanoparticles such as silver, silver conjugate, copper or copper conjugate and gold or gold conjugate nanoparticles. According to the present invention, the polymeric product could contain more than one anti-microbial substance in order to optimize the effect. The substance, which ever it is, should preferably be evenly distributed within functional layer of the polymeric product.

In the present application the nanoparticles are of the size 1-300 nm in diameter; i.e. the particles are 1 nm or more, or more than 20 nm, or more than 50 nm, or more than 100 nm or more than 200 nm, but less than 300 nm or less than 150 nm or less than 70 nm.

The thickness of the protective layer should be thick enough in order to minimize any potential leakage from the anti-microbial substance but thin enough in order to gain more homogenous mechanical properties of the product. The thickness should therefore be between 1-100 µm; i.e. the thickness should be 1 µm or more, or more than 20 µm, or more than 40 µm or more than 80 µm, but less than 100 µm or less 60 µm or less than 30 µm.

A study has shown that the protective layer does not have to be thicker than 1 µm in order to hinder leakage of for example silver particles or ions. Therefore the protective layer may be less than 1 µm, for example 100 nm or more, or 500 nm or more. The protective lay may then have a thickness of 100 nm to 100 µm.

The amount of anti-microbial substance should not affect the properties of the product. When using nanoparticles the concentration should be in the range of 0-10 weight %; i.e. the concentration could be more than 0 weight %, or more than 2 weight %, or more than 5 weight %, or more than 8 weight % but not more than 10 weight % or less than 7 weight % or less than 4 weight %. When using other anti-microbial substances the concentration could be in the range 0 to 10 weight %.

According to the present application, the polymeric product may be a functional product or device or it may be applied as a coating to an already existing product or device.

A preferred embodiment of the present invention comprises a functional layer 20 of polysiloxane rubber containing 0.01-2 weight % silver nanoparticles. The protective layer 30, completely covering the functional layer, would comprise of a polysiloxane rubber layer of 1-10 µm lacking any anti-microbial substances.

Production of the Polymeric Product

The polymer product according to the present invention may be produced by first producing a functional layer. The functional layer may be provided according to any method known to a person skilled in the art including but not limited to, injection moulding, compression moulding, injection reaction moulding, transfer moulding, blow moulding, rotational moulding, extrusion, solvent spinning, dry spinning, film blowing, rotational blowing or calendaring of a polymer material. The anti-microbial substance should preferably be added to the polymer of the functional layer prior to the production of the functional layer. Depending on the anti-microbial substance and the production technique that will be used to produce the functional layer, the substance could be added to a polymer solution, to a melt or to the monomers prior to or during the polymerisation. If the anti-microbial substance comprises metal nanoparticles, the metal nanoparticles can be added to the polymer solution as a colloidal solution in a proper solvent or be synthesized directly in the polymer solution.

The polymer in the functional layer may also be cross-linked, fully or partly. The cross-linking density could be varied depending on the application and the properties wanted. Cross-linking could be achieved using any method known to a person skilled in the art and includes using, cross-linking agents such as peroxides, sulphur, olefins or multifunctional groups, but cross-linking could also be achieved by using heat, radiation or light.

Covering the functional layer with a protective layer could be accomplished using various coating techniques such as dip coating, spin coating or spraying. The protective layer could also be pre-made and thereafter arranged on the functional layer. This could be achieved by wrapping or sliding the pre-made protective layer around or over the functional layer. Alternatively, the polymeric material of the protective layer may be polymerized onto the functional layer. Additionally, the protective layer may also be cross-linked, fully or partly, using any of the methods mentioned above.

The first and the protective layer could also be produced simultaneously by using injection moulding, compression moulding, injection reaction moulding, transfer moulding, blow moulding, rotational moulding, extrusion, film blowing, rotational blowing or calendaring.

When the polymeric product comprises more than two layers, all the layers could be produced according the methods described above. The functional layer, i.e. the layer comprising the anti-microbial substance, could be produced first and then coated with the additional protective layers. This coating could be done using various coating techniques such as dip coating, spin coating or spraying. The protective layers could also be pre-made and thereafter arranged on the functional layer or the polymeric material may be polymerized onto the functional layer.

The order of layer production could be altered, that is, the protective layer could be produced first followed by the functional layer. In this embodiment, the functional layer could be coated on the protective layer using dip coating, spin coating or spraying; or the polymeric material may be polymerized onto the protective layer.

Applications of the Polymeric Product

The construction according to the present invention is applicable to a wide range of applications, for example in vivo applications. In vivo applications could be various implants or devices in contact with tissue. For example, the present invention could be used as voice membrane or prostheses, heart valves, joints, lenses, tendons, breast implants, catheters, membranes, tubes or as an insulation material for leads. However, the present invention is also applicable to non in vivo applications such as sealing or insulation material, gasket, membrane, valves or filters or wherever a polymeric product is exposed to possible microbial attack.

A Kit for Producing the Polymeric Product

In order to provide the layers (i.e. the functional layer with the anti-microbial substance and the protective layer without said substance) on an already made polymeric product, the present invention provides a kit comprising the necessary components.

The kit comprises a plurality of components. The components for the functional layer and for the protective layer may be provided in separate containers for ease of handling.

The components for providing the functional layer comprise at least a polymeric material and an anti-microbial substance. Optionally, the components may further comprise a curing agent, i.e. a cross-linking agent. Each of the components may be provided in a suitable solvent.

The components for providing the protective layer comprise a polymeric material and optionally a curing agent. The components may be provided in a suitable solvent.

Thus, the kit can be said to comprise two sets of components, each providing separate layers.

For example, the kit could comprise of two parts, each containing three and two components respectively. The polymeric material in the first and second part could each be a polymer based on siloxane, isoprene, styrene-butadien, styrene-ethylene, butadiene, butyl, ethylene-propylene, nitrile, acrylic, chloroprene, fluoro silicone, nitrile butadiene, methyl vinyl silicone or urethane. Each polymeric material could be provided in a suitable solvent. The second component in the two parts is a curing agent. This agent could be peroxid, AIBN or any other radical forming substance; or a sulphur component; olefins or multifunctional groups; or a substance capable of forming cross-links when exerting the polymer to heat, radiation or light. The third component in the first part is silver nanoparticles, provided as anti-microbial substance.

In another example, the kit could comprise of two parts, each containing two and one component/s respectively. The polymeric material in the first and second part could each be a polymer based on polyester, polyethers, polyamines, polyamides, polyurethanes, polysiloxanes, polypropylenes, polycarbonates, polyacrylates, polyvinyls, polyethylenes, polyimides, polysulfones, polyfenyloxides, polyacetals, polycellulose and polystyrene. Each polymeric material could be provided in a suitable solvent. The second component in the first part is silver nanoparticles, provided as anti-microbial substance.

Examples

In a first example the inventive polymeric product is used for voice prostheses. Voice prostheses are used by for example patients who have been subjected to laryngectomy and therefore lost their ability to speak. Voice prostheses are usually made of so called medical silicone. A voice prosthesis is placed between trachea and the oesophagus and enables the patient to speak again. The environment in which the voice prosthesis is placed is extremely subjected to microbial (typically fungal) attacks, especially since most of those patient have reduced immune defense. Fungal attacks may result in the afore-mentioned ingrowth and deterioration of the voice prosthesis.

The inventive polymeric product can be made in the form of a voice prosthesis. A voice prosthesis can according to the invention be fabricated according to the following steps:
1. Providing an ordinary voice prosthesis made from silicone, i.e. not coated with the first and second layers according to the invention,
2. providing a first polymeric material containing an anti-microbial substance, preferably silver nanoparticles, on as a first layer on voice prosthesis, e.g. by dip coating,
3. optionally cure the first layer,
4. providing, on said first layer, a second layer completely covering said first layer, wherein the second layer comprises a polymeric material, wherein the second layer does not comprise any anti-microbial substances;
5. optionally cure the second layer.

The first three steps can be replaced by providing a voice prosthesis which is casted (or fabricated by other methods known in the art) using a material with a similar composition as the described first layer, i.e. comprising a polymeric material containing an anti-microbial substance.

The polymeric product described above is protected from fungal ingrowth and the second layer ensure that that a patient using the polymeric product is not exposed to the anti-microbial substance.

In another example the inventive polymeric product is used for catheters, e.g. urinary tract catheters, drain catheters or vein catheters. The fabrication of such catheters can be performed in a similar way as the fabrication of voice prosthesis, as described above. For these applications could for example various polyesters, polyethers or polyurethanes be used, both in the functional layer and in the protective layer.

In other examples the polymeric product is used for implantable devices, such as heart valves, containers for drugs and/or food stuff or building materials. For these applications could for example various polycarbonates, polyacrylates, polyesters, polyethers or polyurethanes be used, both in the functional layer and in the protective layer.

The invention claimed is:
1. An in vivo implant or device for a patient, comprising at least two layers, the at least two layers comprising:
   a functional layer comprising a polymeric material and at least one anti-microbial substance, and
   an outer protective layer comprising a polymeric material arranged outside the functional layer and completely covering said functional layer,
   wherein the protective layer does not comprise any anti-microbial substances,
   the thickness of the protective layer is 1 µm to 30 µm, and
   wherein during use the protective layer shields the patient from the at least one anti-microbial substance.
2. The in vivo implant or device according to claim 1, wherein the anti-microbial substance in the functional layer is metal nanoparticles.
3. The in vivo implant or device according to claim 1, wherein the polymeric materials in the functional and protective layers are rubber and/or thermoplastic elastomer.
4. The in vivo implant or device according to claim 1, wherein the polymeric material in the functional and protective layers is the same.
5. The in vivo implant or device according to claim 1, wherein the polymeric material in at least one of the functional and protective layers is selected from the group consisting of natural rubber, silicone rubber, isoprene rubber, styrene-butadiene rubber, styrene-ethylene rubber, butadiene rubber, butyl rubber, ethylene-propylene rubber, nitrile rubber, acrylic rubber, chloroprene rubber, fluoro silicone rubber, nitrile butadiene rubber, methyl vinyl silicone rubber, urethane rubber, and combinations thereof.
6. The in vivo implant or device according to claim 1, wherein the polymeric material in at least one of the functional and protective layers is selected from the group consisting of polyester, polyethers, polyamines, polyamides, polyurethanes, polysiloxanes, polypropylenes, polycarbonates, polyacrylates, polyvinyls, polyethylenes, polyimides, polysulfones, polyfenyloxides, polyacetals, polycellulose, polyoleophines, polystyrene, and combinations thereof.
7. A device for in vivo applications, comprising the in vivo implant or device of claim 1, wherein the device is configured to have contact with tissue.
8. The device according to claim 7, wherein the in vivo application is as voice membrane, prostheses, heart valves, joints, lenses, tendons, breast implants, catheters, or as an insulation material.
9. The in vivo implant or device according to claim 1, wherein the thickness of the protective layer is 1 µm to 10 µm.
10. The in vivo implant or device according to claim 1, wherein the functional layer comprises more than 0.01 weight % to 2 weight % of the at least one anti-microbial substance.
11. A method of producing the in vivo implant or device of claim 1, comprising the steps of:
   a. providing a first polymeric material containing an anti-microbial substance;
   b. forming a functional layer comprising the first polymeric material;
   c. optionally curing the functional layer;
   d. providing, on said functional layer, a protective layer completely covering said functional layer, wherein the protective layer comprising a polymeric material does not comprise any anti-microbial substances;
   e. optionally curing the protective layer; and optionally
   f. repeating step d and e to provide additional layers.
12. The method according to claim 11, wherein the protective layer is provided using dip coating, spin coating, spraying, compression or injection moulding or wherein the protective layer is preformed and then applied on the functional layer.
13. The method according to claim 11, wherein the functional layer is provided using dip coating, spin coating, spraying, extruding, blowing or moulding techniques.

14. The method according to claim 13, wherein the functional layer is formed using injection moulding, compression moulding, injection reaction moulding, transfer moulding, blow moulding, rotational moulding, film blowing, rotational blowing or calendering.

15. The method according to claim 11, wherein the anti-microbial substance is a metal nanoparticle.

16. The method according to claim 11, wherein the anti-microbial substance is a silver and/or copper nanoparticle.

* * * * *